United States Patent [19]

Astbury et al.

[11] Patent Number: 5,625,111
[45] Date of Patent: Apr. 29, 1997

[54] PROCESS FOR THE PRODUCTION OF MONO-OLEFINS

[75] Inventors: Christopher J. Astbury, London; David C. Griffiths, Surrey; Ian A. B. Reid, London, all of England

[73] Assignee: BP Chemicals Limited, London, England

[21] Appl. No.: 368,720

[22] Filed: Jan. 4, 1995

Related U.S. Application Data

[63] Continuation of Ser. No. 107,128, Aug. 17, 1993, abandoned.

[30] Foreign Application Priority Data

Aug. 20, 1992 [GB] United Kingdom ............. 9217685

[51] Int. Cl.$^6$ ......................................... C07C 4/02
[52] U.S. Cl. ................................. 585/653; 585/648
[58] Field of Search ........................... 585/653, 648, 585/650, 651, 652

[56] References Cited

U.S. PATENT DOCUMENTS

| | | | |
|---|---|---|---|
| 3,562,851 | 2/1971 | Hu | 585/658 |
| 3,765,851 | 10/1973 | White | 585/652 |
| 4,760,210 | 7/1988 | Sweeney | 568/910.5 |
| 4,940,826 | 7/1990 | Font Freide et al. | 585/600 |
| 4,952,743 | 8/1990 | Come | 585/541 |
| 5,105,052 | 4/1992 | Font Freide et al. | 585/651 |

FOREIGN PATENT DOCUMENTS

| | | |
|---|---|---|
| 2039113 | 9/1991 | Canada . |
| 0332289 | 9/1989 | European Pat. Off. . |
| 1113102 | 11/1955 | France . |
| 1292477 | 6/1960 | France . |
| 2723685 | 11/1978 | Germany . |
| 62-47232 | 10/1987 | Japan . |

OTHER PUBLICATIONS

Mitsubishi Chem. Ind KK, J5 2065–203, Nov. 25, 1975. JA–140939. (page unavailable).

*Primary Examiner*—Glenn A. Caldarola
*Attorney, Agent, or Firm*—Nixon & Vanderhye

[57] ABSTRACT

A process for the production of mono-olefins from a hydrocarbon feed containing one or more paraffinic hydrocarbons having at least two carbon atoms, the process comprising partial combustion of a mixture of the hydrocarbon feed and a molecular oxygen-containing gas in contact in a reaction chamber with a catalyst capable of supporting combustion beyond the normal fuel rich limit of flammability to produce heat of reaction, the reaction chamber being adapted such that at least part of the heat of reaction is transferred to the incoming feed and the velocity of the incoming feed is maintained at a value above the burning velocity of the feed mixture.

11 Claims, 2 Drawing Sheets

↑ GAS/LIQUID FLOW

↝ HEAT FLOW

PROCESS FOR THE PRODUCTION OF MONO-OLEFINS

This is Rule 62 continuation of application Ser. No. 08/107,128, filed Aug. 17, 1993, now abandoned.

The present invention relates to a process for the production of mono-olefins.

BACKGROUND OF THE INVENTION

Olefins such as ethylene and propylene are extremely valuable industrial products both as monomers for homo- and co-polymer production and as a basic starting material for the production of other desirable chemicals. Such olefins may be obtained through various processes which include the steam cracking of hydrocarbons such as naphtha and liquid petroleum gas feedstocks or through the dehydrogenation of paraffinic hydrocarbons.

European patent application 0332289 discloses a method for the production of mono-olefins which involves the partial oxidation of paraffinic hydrocarbons. Gaseous paraffinic hydrocarbons are mixed with a molecular oxygen-containing gas and contacted with a catalyst capable of supporting combustion beyond the fuel rich limit of flammability. The process, hereinafter described as autothermal cracking provides an efficient and cost-effective method of producing mono-olefins with yields being in excess of that obtained through the conventional steam cracking technology.

The aforementioned process is successful for gaseous hydrocarbon feeds such as ethane, propane or butane. The process is equally applicable to liquid hydrocarbons such as naphtha, gas oil or vacuum gas oil. The liquid hydrocarbons, however, are commonly preheated and partially vaporised prior to entering the reaction chamber, thus requiring an additional step in the process. A problem associated with vaporisation of liquid hydrocarbons is that the conditions, e.g. high temperature, required to achieve vaporisation of heavier feeds may cause cracking of the hydrocarbons. Additionally, complete vaporisation is difficult to achieve and consequently a fine film of liquid can form on the catalyst which can reduce catalyst activity.

Attempts to overcome the aforementioned problem fall into two general categories. Firstly, additional oxygen may be used to promote the combustion and to raise the temperature of the catalyst. This, however, results in a decrease in the yield of olefins. Alternatively, greater heat may be applied. In addition to the problem of cracking of the hydrocarbons, additional pre-heat may result in flashback or autoignition generating a flame at the fuel/oxygen mixing point. This type of flame generates very high flame temperatures and may result in carbon formation and thus a decrease in the yield of olefins.

DESCRIPTION OF THE INVENTION

We have now developed a method for the production of mono-olefins using partial oxidation of hydrocarbons which can successfully convert both gaseous and liquid paraffinic hydrocarbons. Liquid hydrocarbons can be fed directly into the reactor wherein the heat from the subsequent reaction pre-heats and at least partially vaporises the liquid prior to contact with the combustion catalyst.

Accordingly, the present invention provides a process for the production of mono-olefins from a hydrocarbon feed comprising one or more paraffins having at least two carbon atoms, the process comprising partial combustion of a mixture of the hydrocarbon feed and a molecular oxygen-containing gas in contact in a reaction chamber with a catalyst capable of supporting combustion beyond the normal fuel rich limit of flammability to produce heat of reaction, the reaction chamber being adapted such that at least part of the heat of reaction is transferred to the incoming feed, and the velocity of the incoming feed is maintained at a value above the burning velocity of the feed mixture.

The present invention provides the advantage that the mono-olefinic hydrocarbons may be produced more efficiently through the autothermal cracking of either gaseous or liquid paraffinic hydrocarbons. The process of the present invention is particularly suitable for liquid hydrocarbons. Heat generated within the reaction chamber by combustion of a proportion of the hydrocarbon feed is sufficient to support the cracking reactions thus eliminating the need for external heating supplies. Additionally, in the present invention, the arrangement of the reactor permits excess heat generated within the catalyst bed to pass through the wall of the reaction chamber to the inlet zone, thus heating and/or vaporising the incoming feed.

The process of the present invention assists the vaporisation of liquids which boil above the autoignition temperature without causing a flashback to or autoignition at the mixing point. The hydrocarbon feed and oxygen containing gas are introduced into the reactor at a temperature below the autoignition temperature and fuel-oxygen mixing takes place. The heat of the reaction from the catalyst zone heats the feed mixture and vaporises a significant fraction of the liquid feed before the mixture reaches the catalyst.

Conventionally, autothermal cracking is carried out by combustion of a hydrocarbon and an oxygen containing gas. With gas and liquid feeds, a sufficient amount of oxygen is required to maintain stable reaction conditions. In particular with liquid feeds, the temperature of the catalyst must be maintained at a level to ensure sufficient vaporisation of residual liquid from the catalyst surface to prevent reduction of catalyst activity. This ability depends on the heat transfer efficiency within the reactor. The process of the present invention also utilises combustion of hydrocarbon and oxygen containing gas. Additionally, heat transfer from the reaction zone to the incoming reactants is improved, having the advantage that the amount of unvaporised liquid hydrocarbon reaching the catalyst is minimised, reducing loss of activity. Thus, for liquid feeds, an additional vaporising step is not necessary since these may be fed directly into the reactor, the heat of reaction being sufficient to fully, or at least partially, vaporise the liquid hydrocarbons in situ. A further advantage is therefore that a greater proportion of hydrocarbon may be fed into the reactor in liquid form without extinguishing catalyst activity. Furthermore, less oxygen is required to maintain stable reaction conditions, in particular the catalyst bed temperature and thus the process may be operated at a greater hydrocarbon to oxygen ratio. Consequently, less of the hydrocarbon is required to undergo combustion to generate heat for the cracking reactions, with the additional advantage that concentrations of carbon oxides in the product stream are reduced.

The process of the present invention is carried out in a reactor having a reaction chamber entered through an inlet zone and exited through an outlet zone. The reaction chamber accommodates a catalyst which is capable of supporting flammability. Suitably the reaction chamber surrounds or is surrounded by the inlet zone such that there is a common wall between both zones enabling the transfer of the heat of the reaction from the catalyst bed to the reactants. Alternatively, the reaction chamber may be situated at the end of the inlet zone, the incoming feed being pre-heated or vaporised as it enters the chamber. It is preferred that the walls of the reaction chamber and the inlet zone are arranged in concentric circles. In a preferred embodiment of the reactor suitable for use in the process of the present invention, the inlet zone will form a tube or central channel running through the centre of the reaction chamber and opening into the catalyst chamber at the end of the reactor opposite to the reactant inlet. Alternatively, the walls of the inlet zone and the reaction chamber may be arranged to form parallel adjacent channels, again there being a common wall between the two zones. It is preferred that the gases passing through the inlet zone and the reaction chamber move in mutually opposed directions.

The reactor of the present invention may comprise a single reaction chamber or may comprise a multiplicity of reaction chambers, the reaction chambers being arranged in a matrix.

The process of the present invention is for the production of mono-olefins from a hydrocarbon feed comprising paraffins. The feed may comprise gaseous hydrocarbons, liquid hydrocarbons or a mixture thereof. The process is especially suitable for liquid hydrocarbons. Suitable gaseous hydrocarbons are ethane, propane, butane, or mixtures thereof. Suitable liquid hydrocarbons may include paraffin containing hydrocarbons such as naphtha, gas oil, vacuum gas oil refinery residues, atmospheric residues, vacuum residues or mixtures of liquid hydrocarbons as found in crude or fuel oils.

Additional feed components may be included, if so desired. In particular, hydrogen may be fed with the hydrocarbon feed into the reaction chamber. The presence of hydrogen usually enables enhanced yields of olefins and reduces the formation of carbon dioxide and carbon monoxide. It will of course be understood that the effect of hydrogen will vary with the hydrocarbon feed. Additional gases such as carbon dioxide, methane, nitrogen, carbon monoxide or steam may be co-fed into the reactant stream.

Where the hydrocarbon feed is a liquid hydrocarbon, the feed may be passed directly into the reactor in the liquid state. The feed may be pre-heated if desired. Suitably, the additional co-fed gases such as hydrogen are mixed with the liquid feed. Suitably, the mixture is introduced into the reaction chamber as a fine spray of droplets such that vaporisation and homogeneous mixing may result. Any suitable means may be used for providing a fine spray of liquid. Suitably, the liquid may be passed through a nozzle. The size of the liquid droplets is suitably small to provide a fine spray of liquid. It will of course be understood that small droplets provide a more efficient vaporisation.

Suitably, the liquid hydrocarbon spray is directed towards the reaction chamber. The heat generated within the catalyst by the partial combustion of the hydrocarbon, the oxygen containing gas and, if desired, hydrogen gas, is transferred through the walls of the chamber to cause heating and vaporisation of the atomised liquid hydrocarbon and heating of the feed.

The hydrocarbon feed is mixed with a molecular oxygen-containing gas. Suitably, the gas is oxygen, optionally diluted with an inert gas such as nitrogen. It is preferred to pre-mix the oxygen-containing gas and the paraffinic feed prior to contact with the catalyst. Suitably the amount of oxygen required for the process of the present invention is from 2 to 20%, preferably 4 to 20% of the amount required for complete combustion to carbon dioxide and water.

The velocity of the hydrocarbon and oxygen-containing gas mixture entering the reaction chamber must be maintained at a value above the burning velocity of the feed mixture. This is especially applicable to flammable mixtures i.e. a feed mixture which can propagate a flame freely within a limited range of compositions. It will of course be understood by the person skilled in the art that the gas velocity will vary for different hydrocarbon feeds, pre-heat temperature and stoichiometry. Typically, the velocity of the feed mixture may be suitably greater than 0.5 $ms^{-1}$, preferably greater than 1 $ms^{-1}$. For the purposes of the present invention, velocity is the velocity of the gas through the inlet zone and burning velocity is defined as the measure of unburnt gas velocity at the point of first temperature rise in a flame, perpendicular to the flame front.

The hydrocarbon feed and oxygen-containing gas is contacted with a catalyst which is capable of supporting combustion. The principle role of the catalyst is to stabilise partial combustion of the gaseous mixture which may not otherwise be flammable.

Suitably, the catalyst is a supported platinum group metal. Preferably, the metal is either platinum or palladium or a mixture thereof. Although a wide range of support materials are available, it is preferred to use alumina as the support. The support material may be in the form of spheres, other granular shapes or may be a continuous multichannel ceramic structure, eg a foam. A preferred support for the catalyst is a gamma alumina coated lithium aluminium silicate foam. The support is loaded with a mixture of platinum and palladium by conventional methods well known to those skilled in the art. The resulting compound is then heat treated to 1200° C. before use in the process of the present invention. Optionally the compound may be reduced prior to use as a catalyst. It is preferred to use the catalyst as a fixed bed.

The process of the present invention may suitably be carried out at a temperature of greater than 600° C., preferably greater than 700° C., especially in excess of 750° C. The upper temperature limit may be suitably 1200° C., preferably 1100° C., especially 1000° C.

The hydrocarbon feed and the oxygen-containing gas may be preheated prior to contact with the catalyst. Where the paraffinic hydrocarbon is a gaseous paraffin such as ethane or propane, the gases may be suitably preheated to 200°–500° C. either prior to mixing with the oxygen-containing gas or after mixing. Where the paraffinic hydrocarbon is a liquid, the hydrocarbon may be heated prior to mixing with the molecular oxygen containing gas.

The gaseous feed mixture may be introduced into the reaction chamber under a gas hourly space velocity of suitably greater than 3000 $hr^{-1}$ in order to minimise the formation of carbon oxides. Preferably, the gas hourly space velocity exceeds 10000 $hr^{-1}$, especially greater than 100000 $hr^{-1}$ It will of course be understood that the optimum gas hourly space velocity will depend upon the feed and the pressure. For the purposes of the present invention, gas hourly space velocity is defined as:

$$GHSV = \frac{\text{volume of total feed at } NTP}{\text{Time} \times \text{volume of catalyst bed}}$$

The process may be carried out under atmospheric or elevated pressure. Where it is desired to use elevated pressure, suitably up to 30 bar, preferably up to 40 bar, most preferably up to 50 bar, it is preferred that the reaction products be quenched as they emerge from the reaction chamber to avoid further reactions taking place. Suitably, the reaction products are quenched within 50 milliseconds of formation. It will of course be understood that the time required for quenching the products will depend upon the reaction conditions such as temperature and pressure.

Where elevated pressure is employed, the reaction products may be quenched using rapid heat exchangers of the type familiar in steam cracking technology. Also possible, either additionally or instead of the indirect heat exchangers, a direct quench may be suitably employed. Suitable quenching fluids include water and hydrocarbons. At the aforementioned temperature and pressure, some of the hydrocarbon quenching fluid may be cracked to provide additional olefinic products in the effluent stream. Such hydrocarbon quenching fluids are referred to as reactive quenching fluids. The amount of quenching fluid and choice of fluid which may be usefully employed will depend upon the temperature of the effluent stream. Optionally, a second quenching fluid such as water may be employed if a hydrocarbon fluid is utilised in the process.

The products of the process of the present invention are suitably ethene, propene, butenes and pentenes. In addition to these products, carbon monoxide, aromatic hydrocarbons as well as small amounts of methane, acetylenes, water, hydrogen and carbon dioxide may be produced. The products from the process of the present invention are preferably removed from the reaction chamber rapidly by a high gas flow.

BRIEF DESCRIPTION OF THE DRAWINGS

The invention will now be described by way of example with reference to FIGS. 1 and 2 and the following examples.

In use, the paraffinic hydrocarbon and oxygen are fed into the reactor through inlet (1). The reactants may be mixed either before or after passage through the nozzle (2) into the inlet zone (3). Heat generated from reaction in the catalyst bed is transferred through the common wall (8) to the inlet zone, thus heating the incoming reactants and at least partially vaporising the liquid hydrocarbons. The reactants are then carried through the inlet zone into the reaction chamber for cracking.

Figure 1:
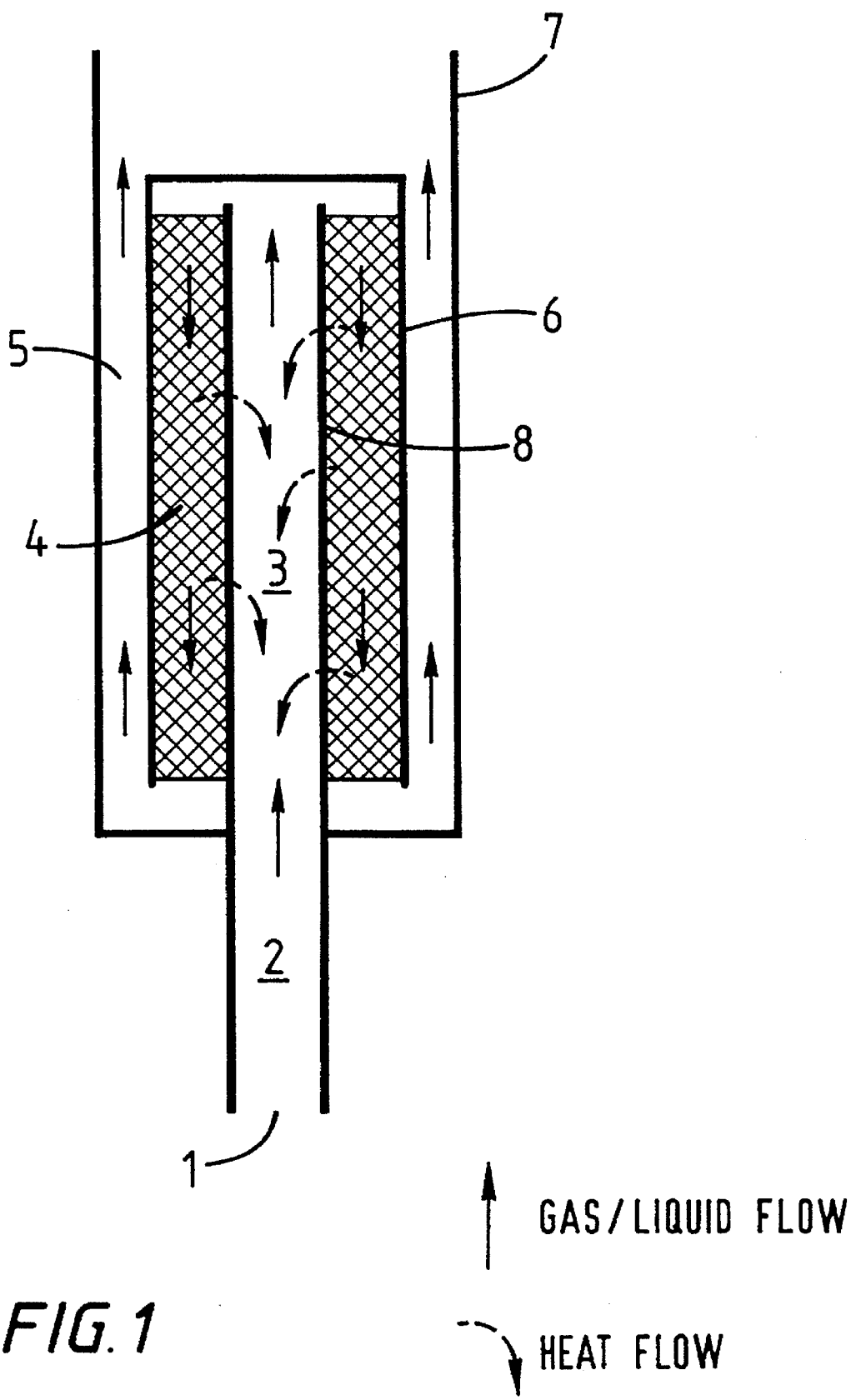
FIG. 1 shows a vertical section through a reactor for producing mono-olefins according to the present invention. Reactant feed is fed through an external inlet (1) and passed through a nozzle (2) into an inlet zone (3) surrounded by a reaction chamber (4) which accommodates a combustion catalyst. Products exit the reactor through an outlet zone (5) which is in the form of an annulus between the outer wall (6) of the reaction chamber (4) and the outer wall (7) of the reactor. The reaction chamber (4) is in the form of a cylinder with the inlet zone (3) located in the inner annulus.
Figure 2:
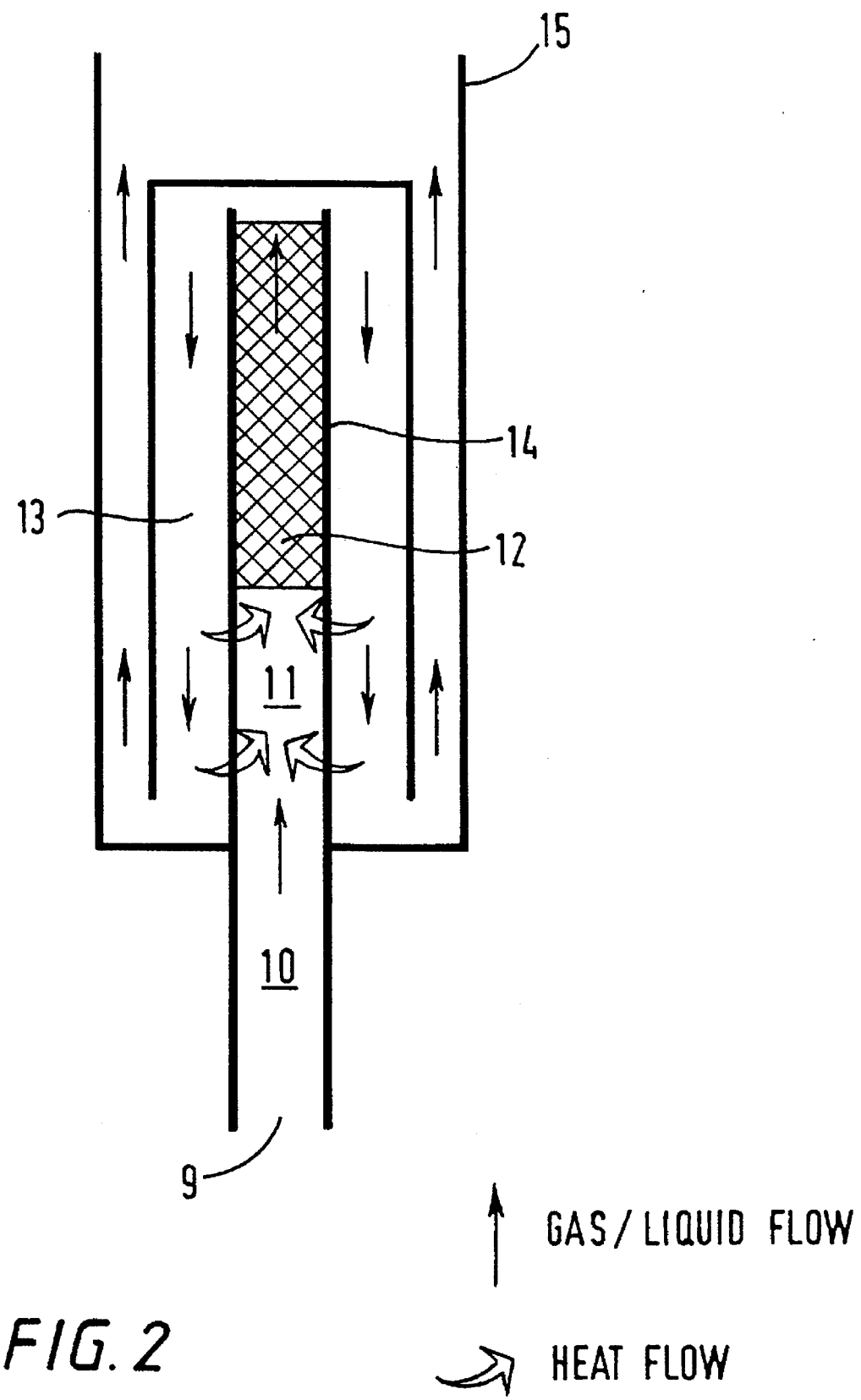

FIG. 2 shows a vertical section through an alternative embodiment. Reactant feed is fed through an external inlet (9) and passed through a nozzle (10) into an inlet zone (11) which precedes the reaction chamber (12) which accommodates the combustion catalyst. Products pass out of the reaction chamber (12) through an outlet zone (13) which is in the form of annular channels between the outer wall (14) of the reaction chamber (12) and the outer wall (15) of the reactor.

In use, the paraffin containing hydrocarbon and oxygen are fed into the reactor through inlet (9). The reactants may be mixed either before or after passage through the nozzle (10) into the inlet zone (11). Products are carried out of the reaction chamber (12) through an outlet zone (13). A portion of the heat contained in the product gas is transferred through wall (14) to heat the incoming feed.

EXAMPLES

Example A—Preparation of Catalyst

The lithium aluminium silicate foam support was obtained precoated with gamma alumina from Morgan Matroc plc. with a porosity of 30 ppi. The foam was washed with a platinum/palladium solution of tetraamine metal chloride salt, drawn through the support by vacuum, dried and finally calcined at 1200° C. for 12 hours. The impregnation of the foam was controlled by monitoring the volume of solution absorbed by the foam to give a loading of 0.25 wt. % in the final catalyst.

Example B—Start-up Procedure at Atmospheric Pressure

The following start-up procedure is employed when using a liquid feed which contains sulphur compounds. At low temperatures, sulphur compounds in a feed can poison the catalyst surface and prevent the reaction taking place. By initiating the reaction with a sulphur free feed such as ethane, the catalyst temperature is raised to a level where sulphur does not poison the catalyst.

The Pt/Pd loaded ceramic foam catalyst was packed into the reaction chamber of the reactor. Ethane (1.71 litres per minute), hydrogen (1.8 litres per minute) and nitrogen (4 litres per minute) were passed into the reactor. Nitrogen was added as an internal standard for subsequent product analysis by gas chromatography and is not required for operation of the process of the present invention. Oxygen was added gradually until the catalyst temperature was seen to rise and continued until the nominal operating temperature of 900° C. was reached. Ethane flow was then increased and if necessary, oxygen flow increased to maintain the operating temperature. When the gas flows through the reactor were sufficiently high (greater than 10 litres per minute), the temperature was allowed to equilibrate.

Example C—Start-up Procedure at Elevated Pressure

The following start-up procedure is employed for the process when using a liquid feed containing sulphur compounds and when carried out at elevated pressure. The Pt/Pd loaded ceramic foam catalyst was packed into the reaction chamber of the reactor. The pressure in the reactor was increased to 5 bar(g) with nitrogen. Ethane (20 litres per minute), hydrogen (16 litres per minute) and nitrogen (21 litres per minute) were passed into the reactor. Nitrogen was added as an internal standard for subsequent product analysis by gas chromatography and is not required for operation of the process of the present invention. Oxygen was added gradually until the catalyst temperature was seen to rise and the oxygen, nitrogen and ethane flows were increased to give a catalyst temperature of approximately 750° C., at the preferred gas velocity. The temperature was allowed to equilibrate and optionally hydrogen was removed.

Example 1—Ethane/Vacuum Gas Oil Feed

When the operating temperature had reached equilibrium as outlined in Example B, a small amount of liquid hydrocarbon (vacuum gas oil) was introduced into the reactor and passed through the nozzle. Ethane and oxygen flows were altered to maintain the required catalyst temperature. The liquid flow was then increased until the required feed rate and temperature were reached. The gas hourly space velocity was 19000 $hr^{-1}$ and oxygen concentration was approximately 4.5% of the amount of oxygen required for complete combustion to carbon dioxide and water, the process was operated at atmospheric pressure.

Samples were extracted at temperatures of 764° C. and 700° C. and product analyses are shown in Table 1. Carbon/oxygen molar ratios of 2 and 2.6 respectively were required to achieve these temperatures, representing very fuel rich mixtures. Selectivity to olefins of 47.7 wt % C. and 41.9 wt. % C respectively were obtained.

Example 2—Vacuum Gas Oil Feed

The procedure of Example 1 was repeated until no ethane was present and vacuum gas oil was the sole hydrocarbon feed. The oxygen flow in this example was 12.8% of the amount required for complete combustion. A sample was extracted at 875° C. and product analysis is also given in Table 1. Selectivity to olefin for the liquid hydrocarbon feed is 43.8 wt % C.

Example 3 Naphtha Feed

When the operating temperature had reached equilibrium as outlined in Example C, a small amount of liquid hydrocarbon (naphtha) was introduced into the reactor and passed through the nozzle at a rate of 39 grams per minute. Ethane and oxygen flow were adjusted to maintain the required catalyst temperature. Ethane was gradually removed and the naphtha flow increased to 49.2 grams per minute while the oxygen flow was adjusted to maintain the catalyst temperature at the required level. The reactor pressure was maintained at 5 bar(g). A sample was extracted at a catalyst temperature of 805° C. under conditions detailed in Table 2. Selectivity to olefinic products was 42 wt. % C.

Comparative Example 1

The procedure of Example 1 was repeated for an ethane/vacuum gas oil feed using the autothermal cracking technology of European Application No. 0332289. The reactor contained the same catalyst as that of the reactor of the present invention (Pt/Pd loaded alumina washcoated lithium aluminium silicate foam) and was operated at a catalyst temperature of 767° C. and 711° C. The process was operated at atmospheric pressure. Feed and product analyses are shown in Table 3. Carbon to oxygen ratio for the process using the reactor as described in EP-A-0332289 were 1.2 and 1.3 thus indicating the conventional reactor requires relatively fuel lean mixtures to maintain a similar catalyst temperature. Temperatures of approximately 880° C. were measured above the catalyst. Olefin selectivity in this example was determined to be 34.8 and 37.2 wt. % C.

It can therefore be seen that olefin selectivities for the process of the present invention are higher for liquid hydrocarbon feed and over a more extensive range of stoichiometries than for the known autothermal cracking process.

TABLE 1

| Feed (g/min) | | | | | C (total) | | | $^+$Max Temp | Conversion (% mol) | | Yield (wt % C) | | | |
| --- | --- | --- | --- | --- | --- | --- | --- | --- | --- | --- | --- | --- | --- | --- |
| VGO | $C_2H_6$ | $O_2$ | $N_2$ | $H_2$ | $C_2$/OIL | /$O_2$ | H/C | (°C.) | *Ethane | *Oxygen | Olefins | ** | Aromatics | CO + $CO_2$ |
| 5.3 | 10.3 | 6.4 | 4.0 | 0.2 | 1.8 | 2.0 | 2.7 | 764 | 63.1 | 99.3 | 47.7 | 5.8 | 1 | 17.9 |
| 5.3 | 10.3 | 5.0 | 4.0 | 0.2 | 1.8 | 2.6 | 2.7 | 700 | 46.8 | 98.5 | 41.9 | 5.1 | 2.0 | 14.9 |
| 4.5 | — | 2.8 | 20.2 | 0.2 | — | 1.4 | 2.3 | 875 | — | 93.9 | 43.8 | 9.1 | 27.4 | 13.5 |

TABLE 2

| Feed (g/min) | | | | | C (total) | | | $^+$Max Temp | Conversion (% mol) | | Yield (wt % C) | | | |
| --- | --- | --- | --- | --- | --- | --- | --- | --- | --- | --- | --- | --- | --- | --- |
| Naphtha | $C_2H_6$ | $O_2$ | $N_2$ | $H_2$ | $C_2$/OIL | /$O_2$ | H/C | (°C.) | *Ethane | *Oxygen | Olefins | ** | Aromatics | CO + $CO_2$ |
| 49.2 | 0 | 24.4 | 52.1 | 0 | — | 1.7 | 2.2 | 805 | — | 99.2 | 42 | 15.9 | 0.6 | 20.1 |

*Conversion = $\frac{\text{ethane in}}{\text{ethane out}} \times 100\%$, $\frac{\text{oxygen in}}{\text{oxygen out}} \times 100\%$
**Ex ethane
$^+$Maximum Temperature measured above the catalyst bed

TABLE 3

| Feed (g/min) | | | | | C (total) | | | $^+$Max- Temp | Conversion (% mol) | | Yield (wt % C) | | | |
| --- | --- | --- | --- | --- | --- | --- | --- | --- | --- | --- | --- | --- | --- | --- |
| VGO | $C_2H_6$ | $O_2$ | $N_2$ | $H_2$ | $C_2$/OIL | /$O_2$ | H/C | (°C.) | *Ethane | *Oxygen | Olefins | ** | Aromatics | CO + $CO_2$ |
| 2.3 | 7.1 | 6.4 | 3.9 | 0.2 | 2.8 | 1.2 | 2.9 | 883 | 96.0 | 96.8 | 34.8 | 8.3 | 3.4 | 22.8 |
| 3.7 | 7.9 | 7.4 | 4.0 | 0.2 | 2.0 | 1.3 | 2.7 | 880 | 92.3 | 96.8 | 37.2 | 7.8 | 5.3 | 22.2 |

*Conversion = $\frac{\text{ethane in}}{\text{ethane out}} \times 100\%$, $\frac{\text{oxygen in}}{\text{oxygen out}} \times 100\%$
**Ex ethane
$^+$Maximum Temperature measured above the catalyst bed

We claim:

1. A process for the production of mono-olefins from a liquid hydrocarbon feed comprising one or more paraffins having at least two carbon atoms, the process comprising the steps of:

partially combusting a mixture of the liquid hydrocarbon feed and a molecular oxygen-containing gas in a reaction chamber with a combustion catalyst;

transferring at least part of the heat of reaction produced during said partial combustion to the incoming feed mixture through the reaction chamber, and maintaining the velocity of the incoming feed mixture at a value above the burning velocity of the feed mixture to produce said mono-olefins.

2. A process according to claim 1 in which the reaction chamber surrounds or is surrounded by an inlet zone such that there is a common wall between said chamber and zone.

3. A process according to claim 2 in which the reaction chamber and the inlet zone are arranged concentrically.

4. A process according to claim 2 in which the inlet zone and reaction chamber are arranged to form parallel adjacent channels.

5. A process according to claim 1 in which the hydrocarbon feed is naphtha, gas oil, vacuum gas oil, refinery residues, atmospheric residues, vacuum residues or mixtures of liquid hydrocarbons as found in crude or fuel oils.

6. A process according to claim 1 in which the catalyst is a platinum group metal on a support.

7. A process according to claim 6 in which the support is alumina.

8. A process according to claim 6 in which the platinum group metal is platinum or palladium or a mixture thereof.

9. A process according to claim 1 in which the hydrocarbon feed and the molecular oxygen-containing mixture comprises from 2 to 20% of the amount of oxygen required for complete combustion to carbon dioxide and water.

10. A process according to claim 1 in which the gas hourly velocity of the hydrocarbon feed is greater than 3000 $hr^{-1}$.

11. A process according to claim 1 wherein the process is operated at a temperature of 600°–1200° C. and under a pressure of 1–50 bar.

* * * * *